United States Patent [19]
Ni et al.

[11] Patent Number: 5,985,601
[45] Date of Patent: Nov. 16, 1999

[54] DNA ENCODING HUMAN CYSTATIN E

[75] Inventors: Jian Ni, Gaithersburg; Guo-Liang Yu, Darnestown; Reiner Gentz, Silver Spring; Craig A. Rosen, Laytonsville, all of Md.

[73] Assignee: Human Genome Sciences, Inc., Rockville, Md.

[21] Appl. No.: 08/461,030

[22] Filed: Jun. 5, 1995

[51] Int. Cl.$^6$ ............................ C12N 15/19; C12N 15/63; C07K 14/52

[52] U.S. Cl. .................... 435/69.1; 435/71.2; 435/252.3; 435/320.1; 435/325; 435/471; 536/23.5; 530/350

[58] Field of Search ................................ 435/69.1, 172.3, 435/240.2, 240.3, 252.3, 320.1, 71.1, 71.2, 325, 471; 536/23.1, 23.5; 530/350; 935/11, 22, 52, 66

[56] References Cited

U.S. PATENT DOCUMENTS

| 5,212,297 | 5/1993 | Colella et al. | 536/24.31 |
| 5,432,264 | 7/1995 | Grubb et al. | 530/350 |

OTHER PUBLICATIONS

J. Biol. Chem., vol. 266, No. 30, issued Oct. 25, 1991, Freije, et al., pp. 20538–20543.
Gene, vol. 61, issued 1987, Saitoh, et al., pp. 329–338.
Biochem. Biophys. Res. Comm., vol. 162, No. 3, issued Aug. 15, 1989, Saitoh, et al., pp. 1324–1331.
Pennacchio, L. A. et al., Science 271: 1731–1733 (1996).
Sotiropoulou, G. et al., J. Biol. Chem., 272: 903–910 (1997).
Sotiropoulou, G. etal., GenBank Accession #HSU62800 Aug. 1996.
Cole et al. (1989) Eur. J. Biochem. vol. 186, pp. 35–42.

*Primary Examiner*—Prema Mertz
*Attorney, Agent, or Firm*—A. Anders Brookes

[57] ABSTRACT

Disclosed is a human CysE polypeptide and DNA (RNA) encoding such polypeptide. Also provided is a procedure for producing such polypeptide by recombinant techniques. Also disclosed are methods for utilizing such polypeptide for treating osteoporosis, tumor metastases, microbial infections, viral infection, septic shock, inflammation, retinal irritation, caries, cachexia and muscle wasting. Diagnostic methods for detecting mutations in the coding sequence and alterations in the concentration of the polypeptides in a sample derived from a host are also disclosed.

14 Claims, 1 Drawing Sheet

```
                  10                     30                      50
  1 ACGGCACTGACGGCCATGGCGCGTTCGAACCTCCCGCTGGCGCTGGGCCTGGCCCTGGTC 60
                    M  A  R  S  N  L  P  L  A  L  G  L  A  L  V 70                     90                     110
 61 GCATTCTGCCTCCTGGCGCTGCCACGCGATGCCCGGGCCCGGCCGCAGGAGCGCATGGTC 120
     A  F  C  L  L  A  L  P  R  D  A  R  A  R  P  Q  E  R  M  V 130                    150                    170
121 GGAGAACTCCGGGACCTGTCGCCCGACGACCCGCAGGTGCAGAAGGCGGCGCAGGCGGCC 180
     G  E  L  R  D  L  S  P  D  D  P  Q  V  Q  K  A  A  Q  A  A 190                    210                    230
181 GTGGCCAGCTACAACATGGGCAGCAACAGCATCTACTACTTCCGAGACACGCACATCATC 240
     V  A  S  Y  N  M  G  S  N  S  I  Y  Y  F  R  D  T  H  I  I 250                    270                    290
241 AAGGCGCAGAGCCAGCTGGTGGCCGGCATCAAGTACTTCCTGACGATGGAGATGGGGAGC 300
     K  A  Q  S  Q  L  V  A  G  I  K  Y  F  L  T  M  E  M  G  S 310                    330                    350
301 ACAGACTGCCGCAAGACCAGGGTCACTGGAGACCACGTCGACCTCACCACTTGCCCCCTG 360
     T  D  C  R  K  T  R  V  T  G  D  H  V  D  L  T  T  C  P  L 370                    390                    410
361 GCAGCAGGGGCGCAGCAGGAGAAGCTGCGCTGTGACTTTGAGGTCCTTGTGGTTCCCTGG 420
     A  A  G  A  Q  Q  E  K  L  R  C  D  F  E  V  L  V  V  P  W 430                    450                    470
421 CAGAACTCCTCTCAGCTCCTAAAGCACAACTGTGTGCAGATGTGATAAGTCCCCGAGGGC 480
     Q  N  S  S  Q  L  L  K  H  N  C  V  Q  M 490                    510                    530
481 GAAGGCCATTGGGTTTGGGGCCATGGTGGAGGGCACTTCACGTCCGTGGGCCGTATCTGT 540

550                    570
541 CACAATAAATGGCCAGTGCTGCTTCTTGCAAAAAAAAAA                       581
```

FIG.1

DNA ENCODING HUMAN CYSTATIN E

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as human cystatin E, sometimes hereinafter referred to as "CysE". The invention also relates to inhibiting the action of such polypeptides.

The cystatin superfamily comprises a group of cysteine proteinase inhibitors which are widely distributed in human tissues and body fluids, and which form tight and reversible complexes with cysteine proteinases such as cathepsins B, H, L, and S. The cystatins are most likely involved in the regulation of normal or pathological processes in which these proteinases participate. Thus, cystatins may influence the intra- and extracellular catabolism of proteins and peptides (Barret, A. J. and Kirchke, H., *Methods Enzymol.*, 80:535–561 (1981)), regulate proteolytic processing of prohormones (Orlowski, M., *Mol. Cell. Biochem.*, 52:49–74 (1983)) and proenzymes (Taugner, R., et al., *Histochemistry*, 83:103–108 (1985)), protect against penetration of normal tissues by malignant cells (Sloane, B. F., *Semin. Cancer Biol.*, 1:137–152 (1990)) or microorganisms (Bjorck, L., et al., *Nature*, 337:385–386 (1989) and Bjorck, L., et al., *J. Virol.*, 64:941–943 (1990)) and modulate local inflammatory processes in rheumatoid arthritis (Mort, J. S., et al., *Arthritis Rheum.*, 27:509–515 (1984)) and purulent bronchiectasis (Buttle, D. J., et al., *Scand. J. Clin. Lab. Invest.*, 50:509–516 (1990)).

The cystatin superfamily has been sub-divided into families I, II and III (also called the stefin, cystatin and kininogen families, respectively), each with members differing from those of the other families in structural organization and biological distribution (Barret, A. J., et al., *Biochem. J.*, 236:312 (1986)). The family I cystatins A and B are small proteins consisting of single polypeptide chains of about 100 amino acid residues without disulfide bridges. The family II cystatins consist of polypeptide chains of approximately 120 amino acid residues with two intra-chain disulfide bonds. Finally, the family III cystatins, the kininogens, display a higher degree of structural complexity characterized by the presence of three family II cystatin-like domains, each with two disulfide bridges at positions homologous to those in family II cystatins (Muller-Esterl, W., et al., *Transbiochem. Sci.*, 11:336–339 (1986)). Family I and II cystatins are mainly present intracellularly and in secretory fluids (Abrahamson, M., et al., *J. Biol. Chem.*, 261:11282–11289 (1986)), whereas kinigogens are highly concentrated in blood plasma (Adam, A., et al., *Clin. Chem.*, 31:423–426 (1985)).

At least one type II cystatin, designated cystatin C, appears to be expressed in all tissues (Abrahamson, M., et al., *Biochem. J.*, 268:287–294 (1990)). In contrast, S-type cystatins are found predominantly in saliva (Abrahamson, M., et al., *J. Biol. Chem.*, 261:11282–11289 (1986)). Cystatins and derivative peptides possess antibacterial and antiviral activities (Bjorck, et al. (1989, 1990)), consistent with their presence in secretions bathing epithelial surfaces directly exposed to the environment. The cystatins may also modulate the immune response. This could occur directly, by inhibiting cysteine proteases releases by macrophages (Bieth, J., *Cysteine Proteinases and Their Inhibitors*, V. Turk, ed. (Walter De Gruyter & Company, New York) pp. 693–703 (1986)), or indirectly, by inhibiting the chemotaxic response and the phagocytosis-associated respiratory burst of the cells (Leung-Tack, et al., *Biol. Chem.*, 371:255–258 (1990)). This data suggests that type II cystatins might perform a variety of protective functions at epithelial surfaces. The human type II cystatin gene family consists of at least seven members.

The disease hereditary cystatin C amyloid angiopathy (HCCAA) is associated with a Glu→Leu mutation in the gene encoding cystatin C. This leads to deposition of amyloid fibrils comprised of this mutant cystatin C in the cerebral arteries, which appears to cause fatal hemorrhaging (Ghiso, J., et al., *PNAS. USA*, 83:2974–2978 (1986)).

The polypeptide of the present invention has been putatively identified as a CysE as a result of amino acid sequence homology to cystatin C. This identification has been made as a result of amino acid sequence homology.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention, including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a human nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, to inhibit cathepsins and prevent osteoporosis, tumor metastases, viral replication, inflammation, purulent bronchiectasis to protect the retina, to prevent leukoencephalopathy, to reduce caries, to treat allergic reactions, to treat cachexia and muscle wasting, and to prevent amyloidosis, and as a antimicrobial agent.

In accordance with yet a further aspect of the present invention, there is also provided nucleic acid probes comprising nucleic acid molecules of sufficient length to specifically hybridize to nucleic acid sequences encoding a polypeptide of the present invention.

In accordance with yet a further aspect of the present invention, there are provided antibodies against such polypeptides.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 illustrates the cDNA and corresponding deduced amino acid sequence of the polypeptide of the present invention. The standard one-letter abbreviation for amino acids is used. Sequencing was performed using a 373 automated DNA sequencer (Applied Biosystems, Inc.).

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 97156 on May 22, 1995.

The ATCC number referred to above is directed to a biological deposit with the ATCC, 12301 Parklawn Drive, Rockville, Md. 20852. The strain is being maintained under the terms of the Budapest Treaty and will be made available to a patent office signatory to the Budapest Treaty.

The polynucleotide of this invention was discovered in a cDNA library derived from primary culture amniotic cells. It is structurally related to the cystatin II superfamily. It contains an open reading frame encoding a protein of 149 amino acid residues of which approximately the first 28 amino acids residues are the putative leader sequence such that the mature protein comprises 121 amino acids. The protein exhibits the highest degree of homology to human cystatin C with 37.273% identity and 49.091% similarity over a 110 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length CysE gene may be used as a hybridization probe for a cDNA library to isolate the full length CysE gene and to isolate other genes which have a high sequence similarity to the CysE gene or similar biological activity. Probes of this type preferably have at least 30 bases and may contain, for example, 50 or more bases. The probe may also be used to identify a cDNA clone corresponding to a full length transcript and a genomic clone or clones that contain the complete CysE gene including regulatory and promotor regions, exons, and introns. An example of a screen comprises isolating the coding region of the CysE gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a CysE polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the CysE genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, $Salmonella$ $typhimurium$; fungal cells, such as yeast; insect cells such as Drosophila S2 and Spodoptera Sf 9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, PBPV, PMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The the polypeptide of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The CysE polypeptide of the present invention may be employed to inhibit human cathepsin enzymes and the resulting pathologies related to the action of these cathepsins. For example, CysE may be employed to treat osteoporosis, behcet disease, hypercalcemia, osteomalicia, allergic skin diseases, allergic rhinitis and allergic purpura.

It is also thought that the cathepsins play a vital role in the metastasizing of tumors and, accordingly, CysE may be employed to prevent tumor metastases.

The CysE polypeptide may be employed as an antimicrobial agent to halt the growth of certain microbial agents, for example, streptococci and to reduce dental caries by reducing the production of acids which contribute to caries.

The CysE polypeptide may also be employed as an antiviral agent to treat infection caused by viruses, for example, to prevent the replication of herpes simplex virus (HSV). The CysE polypeptide may also be employed to protect the retina against attack by the cystein proteinases.

The CysE polypeptide of the present invention may also be employed to treat cachexia and muscle wasting by preventing the action of cysteine proteinases.

The CysE polypeptide may also be employed to modify inflammation, for example, that associated with rheumatoid arthritis, and to treat septic shock. The CysE polypeptide may also be employed to treat purulent bronchiectasis.

The polynucleotides and polypeptides of the present invention may be employed as research reagents and materials for discovery of treatments and diagnostics to human disease.

This invention provides a method for identification of the receptor for the cystatin E polypeptide. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the cystatin E polypeptide, and a cDNA library created from this RNA is divided into pools and used to transfect COS cells or other cells that are not responsive to the cystatin E polypeptide. Transfected cells which are grown on glass slides are exposed to labeled cystatin E polypeptide. The cystatin E polypeptide can be labeled by a variety of means including iodination or inclusion of a recognition site for a site-specific protein kinase. Following fixation and incubation, the slides are subjected to autoradiographic analysis. Positive pools are identified and subpools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Crosslinked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention provides a method of screening compounds to identify those which bind to the cystatin E receptor and induce a second messenger response therefrom.

As an example, a mammalian cell or membrane preparation expressing the cystatin E receptor is incubated in the presence of the compound to be screened. The response of a known second messenger system following interaction of the compound and the receptor is measured and compared to the second messenger response induced by cystatin E. Such second messenger systems include but are not limited to, cAMP guanylate cyclase, ion channels or phosphoinositide hydrolysis.

The polypeptide of the present invention and agonist compounds may be assayed for an ability to inhibit cyteine proteinase activity which assay comprises determining equilibrium constants for dissociation ($K_i$) of cystatin E complexes with papain and human cathepsin B, by continuous rate assays with 10 $\mu$M Z-Phe-Arg-NHMec as substrate in 100 M sodium phosphate buffer (Nicklin, M. J. H., and Barrett, A. J., Biochem. J., 223:245–253 (1984). The buffer contains 1 mM dithiothreitol and 2 mM EDTA and is adjusted to pH 6.5 for papain assay and to pH 6.0 for cathepsin B assays. Cathepsin B is preincubated for 20 min in assay buffer at room temperature before use. The enzyme concentrations in the assays are 0.05–0.25 nM. The highest cystatin E concentration tried in cathepsin B assays is 100 nM. The inhibitor concentrations giving informative inhibition, i.e., resulting in a new steady state rate within 1 hour after addition of inhibitor, are 20–50 nM in the papain assays. Substrate hydrolysis at 37° C. is monitored in a Perkin-Elmer Cetus LS50 fluorometer at excitation and emission wavelengths of 360 and 460 nm, respectively. $K_m$ values for hydrolysis of Z-Phe-Arg-NHMec under the assay are used to compensate obtained apparent $K_i$ values for substrate induced dissociation of inhibitor, by the relationship: Apparent $K_i = K_i(1+[S]/K_m)$.

The polypeptides of the present invention and agonist compounds may be employed in combination with a suitable pharmaceutical carrier. Such compositions comprise a therapeutically effective amount of the polypeptide or agonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or agonists of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The CysE polypeptides and agonist compounds which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E–86, GP+envAm12, and DAN cell lines as described in Miller,

*Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Bukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The disease hereditary cystatin C amaloid angiopathy causes fatal hemorrhaging, and may be associated with Alzheimer's disease, Down's syndrome, Parkinson's, dimentia, and could lead to death before age 40.

This invention, therefore, relates to the use of the CysE gene as a diagnostic. Detection of a mutated form of CysE will allow a diagnosis of a disease similar to HCCAA which results from a mutation in the CysE gene.

Individuals carrying mutations in the human CysE gene may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding CysE can be used to identify and analyze CysE mutations. For example, deletions and insertions can be detected by a change in size of the amplified product in comparison to the normal genotype. Point mutations can be identified by hybridizing amplified DNA to radiolabeled CysE RNA or alternatively, radiolabeled CysE antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of soluble CysE

The DNA sequence encoding CysE, ATCC # 97156, is initially amplified using PCR oligonucleotide primers corresponding to the 5' sequences of the processed CysE protein (minus the signal peptide sequence) and the vector sequences 3' to the CysE gene. Additional nucleotides corresponding to CysE were added to the 5' and 3' sequences respectively. The 5' oligonucleotide primer has the sequence 5' CGCCCATGGCGGCCG CAGGAG 3' (SEQ ID NO:3) contains an NcoI restriction enzyme site followed by CysE coding sequence starting from the presumed terminal amino acid of the processed protein. The 3' sequence 5' CGCAAGCTTTCACATCTGCAAAAAGTTGGC 3' (SEQ ID NO:4) contains complementary sequences to a HindIII site and is followed by CysE coding sequence. The restriction enzyme sites correspond to the restriction enzyme sites on the bacterial expression vector pQE-9 (Qiagen, Inc. Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with NcoI and HindIII. The amplified sequences were ligated into pQE-9 and were inserted in frame with the sequence encoding for the histidine tag and the RBS. The ligation mixture was then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the laci repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D. $^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized CysE was purified from this solution by chromatography on a Nickel-Chelate column under conditions that allow for tight binding by proteins containing the 6-His tag (Hochuli, E. et al., J. Chromatography 411:177–184 (1984)). CysE was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Cloning and expression of CysE using the baculovirus expression system

The DNA sequence encoding the full length CysE protein, ATCC # 97156, was amplified using PCR oligonucleotide primers corresponding to the 5' and 3' sequences of the gene:

The 5' primer has the sequence 5' CGCGGATCCGCCAT-CATGGCGC GTTCGAACCTC 3' (SEQ ID NO:5) and contains a BamHI restriction enzyme site (in bold) followed by an efficient signal for the initiation of translation in eukaryotic cells (Kozak, M., J. Mol. Biol., 196:947–950 (1987) and 18 nucleotides of the CysE gene (the initiation codon for translation "ATG" is underlined).

The 3' primer has the sequence 5' CGCGGATCCTCA-CATCT GCAAAAAGTTGGCTT 3' (SEQ ID NO:6) and contains the cleavage site for the restriction endonuclease BamHI and nucleotides complementary to the 3' non-translated sequence of the CysE gene. The amplified sequences were isolated from a 1% agarose gel using a commercially available kit ("Geneclean," BIO 101 Inc., La Jolla, Calif.). The fragment was then digested with the endonuclease BamHI and then purified again on a 1% agarose gel. This fragment is designated F2.

The vector pA2 (modification of pVL941 vector, discussed below) is used for the expression of the CysE protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonuclease BamHI. The polyadenylation site of the simian virus (SV)40 is used for efficient polyadenylation. For an easy selection of recombinant virus the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2, such as pRG1 pAc373, pVL941 and pAcIM1 (Luckow, V. A. and Summers, M. D., Virology, 170:31–39).

The plasmid was digested with the restriction enzyme BamHI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E.coli HB101 cells were then transformed and bacteria identified that contained the plasmid (pBacCysE) with the CysE gene using the enzyme BamHI. The sequence of the cloned fragment was confirmed by DNA sequencing.

5 µg of the plasmid pBacCysE was co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacCysE were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-CysE at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 3

Expression of Recombinant CysE in COS cells

The expression of plasmid, CysE HA is derived from a vector pcDNAI/Amp (Invitrogen) containing: 1) SV40 origin of replication, 2) ampicillin resistance gene, 3) E.coli replication origin, 4) CMV promoter followed by a polylinker region, an SV40 intron and polyadenylation site.

A DNA fragment encoding the entire CysE precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding CysE, ATCC # 97156, was constructed by PCR on the original EST cloned using two primers: the 5' primer 5' GCGCGGATCCACCATG-GCGCGTTCG 3' (SEQ ID NO:7) contains a BamHI site followed by 12 nucleotides of CysE coding sequence starting from the initiation codon; the 3' sequence 5' GCGCTCTAGATCAAGCGTAGTCTGG-GACGTCGTATGGGTACAT CTGCACAAA 3' (SEQ ID NO:8) contains complementary sequences to an XbaI site, translation stop codon, HA tag and nucleotides of the CysE coding sequence (not including the stop codon). Therefore, the PCR product contains a BamHI site, CysE coding sequence followed by HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into *E. coli* strain SURE (available from Stratagene Cloning Systems, 11099 North Torrey Pines Road, La Jolla, Calif. 92037) approximately ten pieces are placed in each flask. The flask the transformed culture was plated on ampicillin media plates and resistant colonies were selected. Plasmid DNA was isolated from transformants and examined by restriction analysis for the presence of the correct fragment. For expression of the recombinant CysE, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the CysE HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

EXAMPLE 4
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleotide sequence selected from the group consisting of:
   (a) a nucleotide sequence encoding amino acid −28 to 121 of SEQ ID NO:2;
   (b) a nucleotide sequence encoding amino acid 1 to 121 of SEQ ID NO:2;
   (c) a nucleotide sequence encoding at least 30 contiguous amino acids of SEQ ID NO:2; and
   (d) the complement of (a), (b) or (c).

2. The isolated polynucleotide of claim 1 wherein said member is (a).

3. The isolated polynucleotide of claim 1 wherein said member is (b).

4. The isolated polynucleotide of claim 1 wherein said member is (c).

5. The isolated polynucleotide of claim 1, wherein the polynucleotide is DNA.

6. The isolated polynucleotide of claim 1, wherein said polynucleotide is RNA.

7. A method of making a recombinant vector comprising inserting the isolated polynucleotide of claim 1 into a vector, wherein said polynucleotide is DNA.

8. A recombinant vector comprising the polynucleotide of claim 1, wherein said polyniucleotide is DNA.

9. A recombinant host cell comprising the polynucleotide of claim 1, wherein said polynucleotide is DNA.

10. The isolated polynucleotide of claim 1 comprising nucleotides 16 to 462 of SEQ ID NO:1.

11. A method for producing a human cystatin E polypeptide comprising expressing the polynucleotide of any one of claims 2, 3 or 4 in a recombinant cell and recovering the polypeptide encoded thereby.

12. An isolated polynucleotide comprising a nucleotide sequence selected from the group consisting of:
   (a) a nucleotide sequence encoding the same mature polypeptide encoded by the human cDNA in ATCC Deposit No. 97156, and
   (b) the complement of (a).

13. The isolated polynucleotide of claim 12, wherein the member is (a).

14. The isolated polynucleotide of claim 12, wherein said polynucleotide comprises DNA identical to the coding portion of the human cDNA in ATCC Deposit No. 97156 which encodes a mature polypeptide.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 581 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 16..462

(ix) FEATURE:
        (A) NAME/KEY: mat_peptide
        (B) LOCATION: 100..462

(ix) FEATURE:
        (A) NAME/KEY: sig_peptide
        (B) LOCATION: 16..99

(xi) SEQUENCE DESCRIPTION: SEQ ID NO:1:

```
ACGGCACTGA CGGCC ATG GCG CGT TCG AAC CTC CCG CTG GCG CTG GGC CTG        51
              Met Ala Arg Ser Asn Leu Pro Leu Ala Leu Gly Leu
              -28         -25                 -20

GCC CTG GTC GCA TTC TGC CTC CTG GCG CTG CCA CGC GAT GCC CGG GCC        99
Ala Leu Val Ala Phe Cys Leu Leu Ala Leu Pro Arg Asp Ala Arg Ala
    -15                 -10                  -5

CGG CCG CAG GAG CGC ATG GTC GGA GAA CTC CGG GAC CTG TCG CCC GAC       147
Arg Pro Gln Glu Arg Met Val Gly Glu Leu Arg Asp Leu Ser Pro Asp
  1           5                  10                  15

GAC CCG CAG GTG CAG AAG GCG GCG CAG GCG GCC GTG GCC AGC TAC AAC       195
Asp Pro Gln Val Gln Lys Ala Ala Gln Ala Ala Val Ala Ser Tyr Asn
             20                  25                  30

ATG GGC AGC AAC AGC ATC TAC TAC TTC CGA GAC ACG CAC ATC ATC AAG       243
Met Gly Ser Asn Ser Ile Tyr Tyr Phe Arg Asp Thr His Ile Ile Lys
             35                  40                  45

GCG CAG AGC CAG CTG GTG GCC GGC ATC AAG TAC TTC CTG ACG ATG GAG       291
Ala Gln Ser Gln Leu Val Ala Gly Ile Lys Tyr Phe Leu Thr Met Glu
     50                  55                  60

ATG GGG AGC ACA GAC TGC CGC AAG ACC AGG GTC ACT GGA GAC CAC GTC       339
Met Gly Ser Thr Asp Cys Arg Lys Thr Arg Val Thr Gly Asp His Val
 65                  70                  75                  80

GAC CTC ACC ACT TGC CCC CTG GCA GCA GGG GCG CAG CAG GAG AAG CTG       387
Asp Leu Thr Thr Cys Pro Leu Ala Ala Gly Ala Gln Gln Glu Lys Leu
                 85                  90                  95

CGC TGT GAC TTT GAG GTC CTT GTG GTT CCC TGG CAG AAC TCC TCT CAG       435
Arg Cys Asp Phe Glu Val Leu Val Val Pro Trp Gln Asn Ser Ser Gln
             100                 105                 110

CTC CTA AAG CAC AAC TGT GTG CAG ATG TGATAAGTCC CCGAGGGCGA             482
Leu Leu Lys His Asn Cys Val Gln Met
            115                 120

AGGCCATTGG GTTTGGGGCC ATGGTGGAGG GCACTTCACG TCCGTGGGCC GTATCTGTCA     542

CAATAAATGG CCAGTGCTGC TTCTTGCAAA AAAAAAAA                             581
```

(2) INFORMATION FOR SEQ ID NO:2:

(i) SEQUENCE CHARACTERISTICS:
        (A) LENGTH: 149 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Arg Ser Asn Leu Pro Leu Ala Leu Gly Leu Ala Leu Val Ala
-28             -25                 -20                 -15

Phe Cys Leu Leu Ala Leu Pro Arg Asp Ala Arg Ala Arg Pro Gln Glu
        -10                  -5                   1

Arg Met Val Gly Glu Leu Arg Asp Leu Ser Pro Asp Asp Pro Gln Val
  5              10                  15                  20

Gln Lys Ala Ala Gln Ala Ala Val Ala Ser Tyr Asn Met Gly Ser Asn
             25                  30                  35

Ser Ile Tyr Tyr Phe Arg Asp Thr His Ile Ile Lys Ala Gln Ser Gln
             40                  45                  50

Leu Val Ala Gly Ile Lys Tyr Phe Leu Thr Met Glu Met Gly Ser Thr
             55                  60                  65

Asp Cys Arg Lys Thr Arg Val Thr Gly Asp His Val Asp Leu Thr Thr
             70                  75                  80

Cys Pro Leu Ala Ala Gly Ala Gln Gln Glu Lys Leu Arg Cys Asp Phe
 85              90                  95                 100

Glu Val Leu Val Val Pro Trp Gln Asn Ser Ser Gln Leu Leu Lys His
                105                 110                 115

Asn Cys Val Gln Met
            120
```

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CGCCCATGGC GGCCGCAGGA G                                          21

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGCAAGCTTT CACATCTGCA AAAAGTTGGC                         30

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGCGGATCCG CCATCATGGC GCGTTCGAAC CTC                    33

(2) INFORMATION FOR SEQ ID NO:6:

(i) SEQUENCE CHARACTERISTICS:
        (A) LENGTH: 32 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

CGCGGATCCT CACATCTGCA AAAAGTTGGC TT                                      32

(2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GCGCGGATCC ACCATGGCGC GTTCG                                              25

(2) INFORMATION FOR SEQ ID NO:8:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

GCGCTCTAGA TCAAGCGTAG TCTGGGACGT CGTATGGGTA CATCTGCACA AA                52
```